United States Patent
Günter et al.

(10) Patent No.: US 10,139,353 B2
(45) Date of Patent: Nov. 27, 2018

(54) APPARATUS AND METHOD FOR EXAMINING COMPONENTS COMPRISING LAID FIBER COMPOSITE FABRICS OR WOVEN FIBER COMPOSITE FABRICS

(71) Applicant: Volume Graphics GmbH, Heidelberg (DE)

(72) Inventors: Thomas Günter, Heidelberg (DE);
Christoph Poliwoda, Mannheim (DE);
Christof Reinhart, Heidelberg (DE);
Tobias Dierig, Heidelberg (DE)

(73) Assignee: VOLUME GRAPHICS GMBH, Heidelberg (DE)

( * ) Notice: Subject to any disclaimer, the term of this patent is extended or adjusted under 35 U.S.C. 154(b) by 31 days.

(21) Appl. No.: 15/111,402

(22) PCT Filed: Jan. 14, 2015

(86) PCT No.: PCT/EP2015/000047
§ 371 (c)(1),
(2) Date: Jul. 13, 2016

(87) PCT Pub. No.: WO2015/106964
PCT Pub. Date: Jul. 23, 2015

(65) Prior Publication Data
US 2016/0349193 A1 Dec. 1, 2016

(30) Foreign Application Priority Data
Jan. 15, 2014 (DE) .................. 10 2014 100 419

(51) Int. Cl.
*G01N 23/046* (2018.01)

(52) U.S. Cl.
CPC ..... *G01N 23/046* (2013.01); *G01N 2223/615* (2013.01)

(58) Field of Classification Search
CPC .............. G01N 23/046; G01N 2223/615
(Continued)

(56) References Cited

U.S. PATENT DOCUMENTS

| 5,841,892 A * | 11/1998 | McGrath | G06T 7/73 345/424 |
|---|---|---|---|
| 6,028,910 A * | 2/2000 | Kirchner | G01N 23/046 378/21 |

(Continued)

FOREIGN PATENT DOCUMENTS

DE    10 2008 046698    3/2010

OTHER PUBLICATIONS

Hassler U et al: "Computed tomography for analysis of fibre distribution in carbonin carbon fibre preforms",Insight (Non-Destructive Testing and Condition Monitoring), British Institute of Non-Destr. Test., Northampton, GB, vol. 50, No. 6, Jun. 1, 2008, pp. 312-315, XP002560085, ISSN: 1354-2575, DOI: 10.1784/INSI. 2008.50.6.312. the whole document.
(Continued)

*Primary Examiner* — Mekonen Bekele
(74) *Attorney, Agent, or Firm* — Shlesinger Arkwright & Garvey LLP (57) ABSTRACT

An apparatus for examining components comprising laid fiber composite fabrics or woven fiber composite fabrics which comprise a number of thin plies with in part different alignment, comprises a measuring device for carrying out a non-destructive measurement to collect volumetric data of the component and comprising an evaluation device for evaluating the collected data of the component, wherein the evaluation by the evaluation device comprises selecting a first analysis region in the collected data of the component, determining a local coordinate system of the first analysis region, successively establishing local material properties
(Continued)

layer-by-layer at predetermined distances in a direction perpendicular to the lateral extent of the first analysis region, detecting ply boundaries along the established material properties, and averaging the local material properties in each detected ply.

19 Claims, 5 Drawing Sheets

(58) Field of Classification Search
USPC .......................................................... 382/176
See application file for complete search history.

(56) References Cited

U.S. PATENT DOCUMENTS

| | | | |
|---|---|---|---|
| 9,278,378 B2* | 3/2016 | Lehmann | G01N 23/18 |
| 9,536,336 B2* | 1/2017 | Shiraki | A61B 6/4064 |
| 2011/0282181 A1* | 11/2011 | Wang | A61B 5/0095 |
| | | | 600/407 |
| 2012/0139540 A1* | 6/2012 | Flood | D06F 39/00 |
| | | | 324/309 |
| 2014/0119497 A1* | 5/2014 | Guzman | E21B 49/02 |
| | | | 378/5 |
| 2015/0053627 A1* | 2/2015 | Silin | B01D 29/00 |
| | | | 210/767 |
| 2015/0377839 A1* | 12/2015 | Jack | G01N 29/4472 |
| | | | 702/33 |

OTHER PUBLICATIONS

Gennadiy Nikishkov et al: "Finite element mesh generation for composites with ply waviness based on X-ray computed tomography" Advances in Engineering Software, vol. 58, Apr. 1, 2013, pp. 35-44, XP055107407XP055107407 ISSN: 0965-9978, DOI: 10.1016/j.advengsoft.2013.01.002. the whole document.

Kurt Schueler and Richard Hale; Object-Oriented Implementation of an Integrated Design and Analysis Tool for Fiber Placed Structures; AIAA-2002-1223;University of Kansas.

Dennis Maier, Tobias Dierig, Christof Reinhart, Thomas Günther; Analysis of Woven Fabrics and Fiber Composite Material Aerospace Parts using industrial CT Data; 5th International Symposium on NDT in Aerospace, Nov. 13-15, 2013, Singapore; Dr. Tobias Dierig, Benjamin Becker, Christof Reinhart, Thomas Günther; Fiber Composite Material Analysis in Aerospace Using CT Data; 4th International Symposium on NDT in Aerospace 2012—We.2.A.3.

* cited by examiner

APPARATUS AND METHOD FOR EXAMINING COMPONENTS COMPRISING LAID FIBER COMPOSITE FABRICS OR WOVEN FIBER COMPOSITE FABRICS

TECHNICAL FIELD

The present invention relates to an apparatus and a method for examining components comprising laid fiber composite fabrics or woven fiber composite fabrics.

DESCRIPTION OF THE PRIOR ART

The non-destructive examination of objects or articles (material or product examinations in the industrial field, medical examinations) is already widespread. By way of example, it is known to examine the internal structures of components, e.g. fiber-reinforced lightweight components in the area of injection molding, using data collected by computed tomography (CT data) in order to obtain information about the fiber distribution and alignment, as these constitute decisive factors for the mechanical properties of the part to be manufactured. In particular, the shear modulus and Young's modulus are strongly influenced by the internal fiber structure.

Such an analysis of fiber-reinforced components provides, inter alia, values for the local fiber orientation and the fiber density for each spatial point in the data record. By way of example, the local orientation can be present here as a 3D orientation (second-order tensor) and directly visualized and evaluated. However, it is also possible to project the 3D orientation onto a user-defined plane or to compare it to a specific reference direction. By way of example, the results can then be visualized as a color superposition representing local orientations. This analysis of a region of interest of the component with a known nominal fiber orientation enables a comparison between the nominal and real orientations. In order to understand the distribution of the fiber orientation along a given coordinate axis (e.g. perpendicular to the surface of the component), it is possible to calculate averaged orientation tensors layer-by-layer in any direction.

In order to calculate the local parameters such as orientation and fiber density, data values from surroundings about each spatial point are used for said point. These surroundings are selected in a manner dependent on the structure to be examined, usually they are selected so large that the influences of the image noise always present in the image data are suppressed by this intrinsic averaging.

In order e.g. in the area of injection molding of fiber-reinforced plastics to obtain a direct comparison between a simulation and real data, it is possible to import the specific simulation grid used for the simulation directly into the visualization/analysis software. The analysis then calculates averaged values of the local fiber orientation and also the fiber/matrix ratio for each individual grid cell. This enables the direct comparison between calculated and simulated values without mapping error. Using the simulation grid as a basis for averaging the local orientations, a comparison between the simulated and measured orientations becomes very accurate.

Lightweight components which are exposed to high demands are based on fiber-reinforced composite materials in the form of laid or woven fabrics, which serve to absorb the high deformation forces which occur. Here, drastic and complicated warps and deformations of the fabrics and the plies thereof occur in partly complexly curved and bent geometries.

However, the previously known methods are not suitable for examining woven and laid fabric plies since these materials, in contrast to the fiber-reinforced materials in the area of injection molding described at the outset, have a ply or fabric structure and the material properties change significantly from ply to ply. Moreover, the plies are generally very thin and the positions thereof are not known well enough in advance. The methodology described in the prior art and the type of averaging present therein lead to erroneous results when analyzing woven and laid fabrics.

SUMMARY OF THE INVENTION

According to the invention, an apparatus for examining components comprising laid fiber composite fabrics or woven fiber composite fabrics which comprise a number of thin plies with in part different alignment, comprising the features as disclosed herein and a method for examining components comprising laid fiber composite fabrics or woven fiber composite fabrics, comprising the features as disclosed herein.

The invention is based on the insight of calculating characteristic properties in the plies of a composite component in order to obtain an automatic identification of different laid or woven fabric plies on the basis thereof.

According to the invention, a non-destructive measurement is initially carried out in order to collect volumetric data of the component to be examined. The goal of this measurement lies in the provision of a record of image data, on the basis of which the further calculations can be carried out. By way of example, these can be data collected by means of computed tomography (CT data records). By way of example, the calculations are carried out on the basis of the grayscale values of the collected data.

Next, a first local analysis region is selected in the collected data of the component and a local coordinate system is determined in the first local analysis region. To this end, it is possible, for example, to use a calculation of the ply or surface normal, for example from the real component geometry, an estimate of the ply structure, from a simulation mesh or the like. Proceeding from the established orientation, local material properties are established successively and layer-by-layer at predetermined distances in a direction perpendicular to the extent of the analysis region. The established values of the local material properties are scanned in order to detect ply boundaries along the established material properties. Finally, the local material properties are averaged in each detected ply.

The lateral dimensions of the analysis region can be selected in a manner dependent on an established curvature of the analysis region. Regions without curvature, or with only little curvature, can be selected to be relatively large, while regions with strong curvature are selected to be relatively small (to the extent that the layers within the plies themselves are not curved, only have little curvature, or the curvature of the layers within the plies differs significantly from the component curvature). The analysis regions can be selected to be relatively large in the case where the layers also have a curvature of at least a similar order to the component curvature. The terms "relatively large" and "relatively small" selected here should not be understood to be relative terms which are oriented to a dimension, but rather within the meaning of "relatively large regions" and "relatively small regions" compared to the component to be examined. Spirit and purpose consists of keeping the measurement inaccuracy of the selected analysis regions as small as possible. The selection of the dimensions of the analysis regions becomes accessible to a person skilled in the art in this context.

Ply boundaries can be detected by detecting discontinuities or minima along the profile curve of local material properties.

Regions around the detected ply boundaries can be weighted differently from the plies themselves in the step of averaging the local material properties for each detected ply. In the extreme case (in particular in the case of very strong discontinuities), these transition or boundary regions can be completely omitted.

Material properties within the aforementioned sense can be, in a mathematical representation, e.g. the mathematical form of scalars, vectors and/or tensors. They can be gray-scale values, standard deviations or variances, orientations or structure tensors, porosity and the like.

The averaging according to the invention can be e.g. a mean value formation, a calculation of higher moments, a histogram distribution, a distribution calculation or the like.

Hence, according to the invention, an automatic separation of the individual plies of the component to be examined is obtained in the original data record, followed by an analysis of the isolated individual plies, likewise in the original data record.

The present description also covers a computer program with program code which is suitable to carry out a method according to the invention when the computer program is executed on an evaluation computer. Both the computer program itself and the former stored on a computer-readable medium (computer program product) are claimed.

Further advantages and refinements of the invention emerge from the description and the attached drawing.

It is understood that the features mentioned above and yet to be explained below can be used not only in the respectively specified combination, but also in other combinations or on their own, without departing from the scope of the present invention.

The invention is schematically illustrated in the drawing on the basis of an exemplary embodiment and it is described in detail below, with reference being made to the drawing.

DETAILED DESCRIPTION

In the figures, the same elements, and also elements with the same function, are denoted by the same reference signs.

Figure 6:
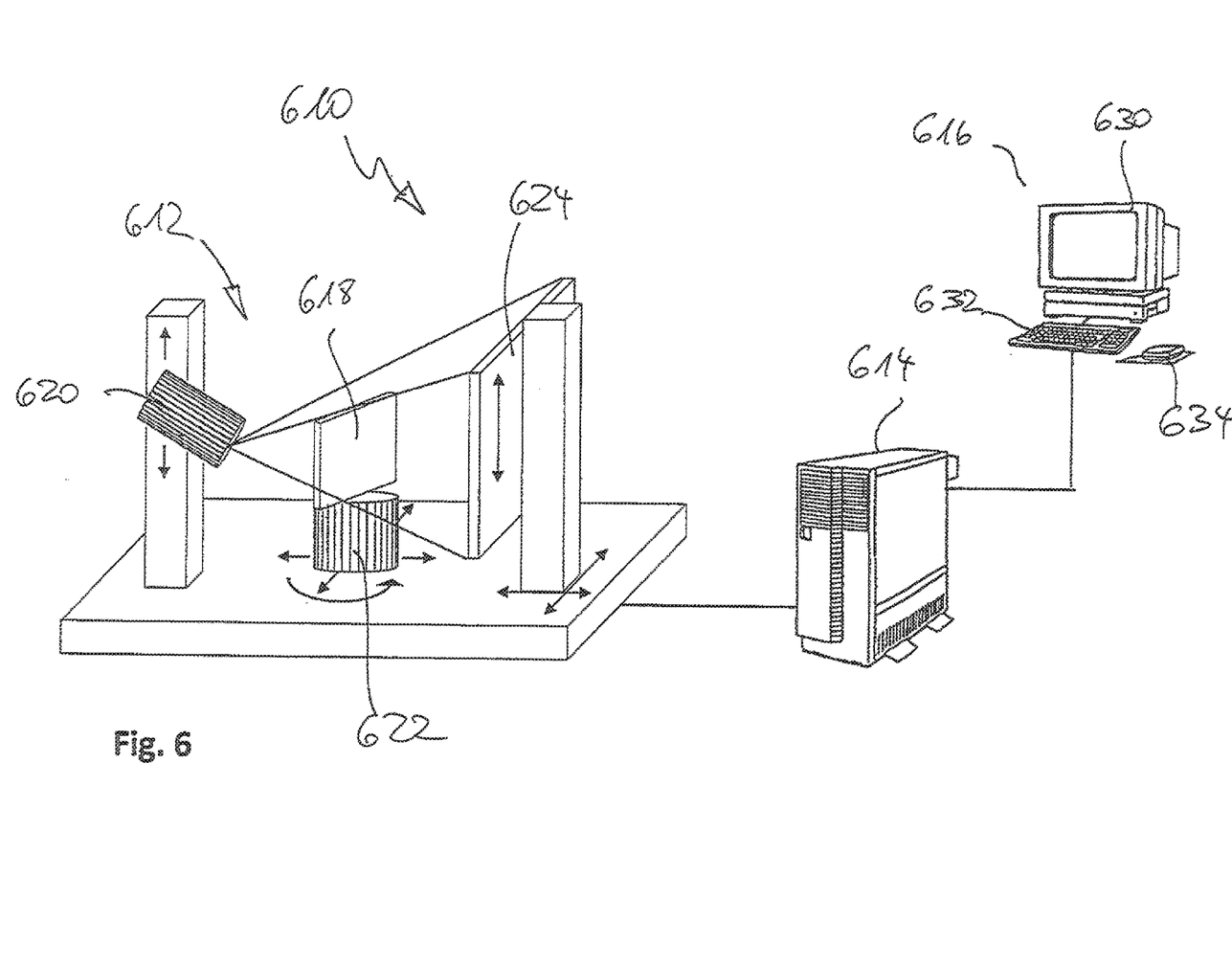
FIG. 6 shows a very schematic illustration of an apparatus according to the invention for examining components.

FIG. 6 shows an apparatus 610 according to the invention for examining components, comprising a measuring device 614 for carrying out a non-destructive measurement on a component 618. The measuring device 614 depicted in an exemplary manner is a computed tomography apparatus comprising an x-ray source 620. The test object or component 618 is arranged on a so-called manipulator or rotary table 622, by means of which x-ray radiation from the x-ray source 620 can pass through the component 618 in different directions. The radiation emerging from the component 618 is recorded by a detector 624. X-ray source 620, rotary table 622 and detector 624 can be displaced and/or rotated within the meaning of the plotted arrows.

The apparatus 610 moreover comprises, in a known manner, an evaluation device 614 for evaluating the measurement data supplied by the detector 624. In order to output the evaluated data, provision is made of an output/input apparatus 616, which, in a conventional manner, has at least one screen 630, a keyboard 632 and, where necessary, a cursor control (mouse) 634. The computer representing the evaluation device 614 can moreover be configured in such a way that it can also control the measuring device 610.

Figure 1:
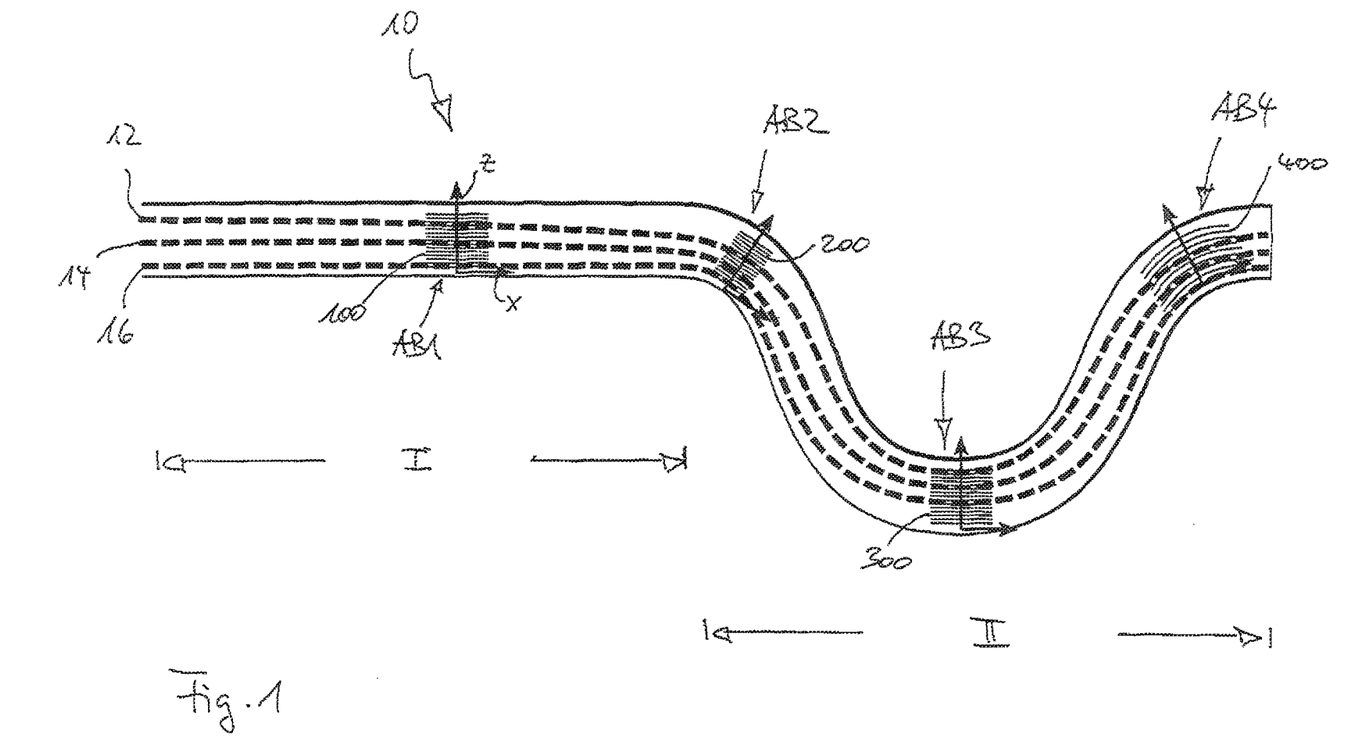
FIG. 1 shows a very schematic sectional illustration through a component with woven fabric plies with different curvatures.

FIG. 1 elucidates the procedure according to the invention using the example of a sectional illustration of a substantially planar component 10 with woven fabric plies 12, 14, 16, with the component 10 having regions with different curvature. The section corresponds to an analysis plane of the component perpendicular to the woven fabric plies.

The component 10 comprises a substantially planar portion I, lying to the left in the illustration of the figure, and a portion II adjoining it on the right, which has a substantially U-shaped cross section, as a result of which various regions with different curvature arise.

The component 10 comprises a plurality of woven fabric plies 12, 14, 16, which extend substantially parallel to one another. Three woven fabric plies are depicted for illustrative purposes; however, more than three plies may also be present. The interstices between the woven fabric plies are likewise for reasons of illustration—depicted in a greatly superelevated fashion.

In principle, there is little curvature of the woven fabric plies 12, 14, 16 in the substantially planar portion I, and so a local analysis region AB1 can be selected to be relatively large (within the meaning of the lateral extent of the ply) in this portion.

The further analysis, according to the invention, of the ply setup of the component in the evaluation device 614 is carried out on the basis of the selected analysis region. The analysis region is a volume region which represents a portion of the collected volumetric data and which is defined by a dimension of extent and an applied local ply coordinate system, wherein the ply coordinate system defines a lateral direction x, which orients itself along the course of the plies, usually substantially parallel to the surface of the component, and an axial direction z. In the depicted exemplary embodiment, the axial direction z extends substantially perpendicular to the lateral direction x.

Naturally, different ply coordinate systems to the described Cartesian system are conceivable, in particular e.g. in conjunction with an analysis region which has curved plies, as is still described below.

According to the invention, analysis layers 100 are defined perpendicular to the axial direction z (or parallel to the lateral direction x) in the analysis region AB1, said analysis layers extending substantially parallel to one another. The analysis layers 100 are selected with a predetermined or set layer thickness, e.g. dependent on the voxelization (i.e. the volumetric grid from recording the volumetric data). By way of example, the layer thickness can correspond to a half voxel resolution. However, in order to obtain good evaluation results, the layer thickness should be selected in such a way that at least two to three layer thicknesses emerge per woven or laid fabric ply of the component.

The analysis layers are thereupon scanned or examined successively in the z-direction in respect of the local material properties in the analysis layer. The material properties established for each analysis layer result in a material property profile along the z-direction, on the basis of which with a material transition or a material change can be established. Ply boundaries (potential boundary planes between plies of the component adjoining one another) can be detected on the basis of these points. Here, possibly available "a priori knowledge", i.e. knowledge about the structure of the component to be examined, such as e.g. ply number, ply thickness or the like, which is available independently of the measurement to be processed, can be used for stabilizing the detection of the ply boundaries. The so-called local material properties are then averaged by forming an average within the ply boundaries established thus in order to form a detected ply.

Figure 2:
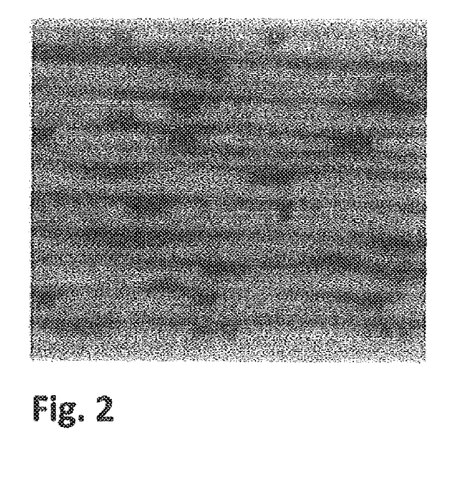
FIG. 2 shows an image with a greatly magnified section through a component with a sequence of (uncompacted) woven fabric plies.
Figure 3:
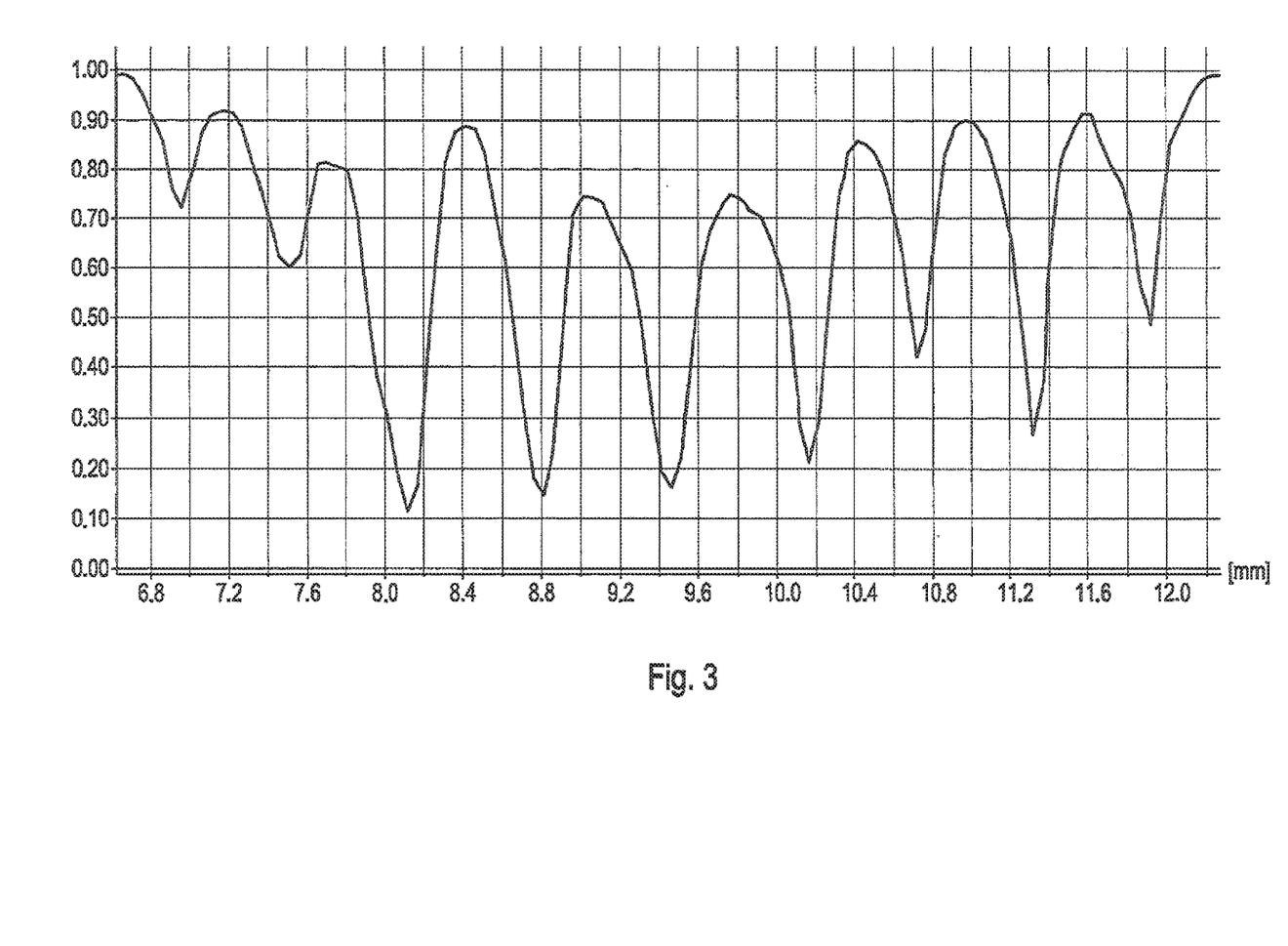
FIG. 3 shows a diagram with a fiber volume portion, determined in accordance with the invention, plotted against the component thickness.

This procedure is shown in an exemplary manner on the basis of FIGS. 2 and 3. FIG. 2 shows a sectional photo of a greatly magnified record of a component with a sequence of woven fabric plies. For improved clarity, this is an uncompacted component, i.e. a component whose woven fabric plies were not pressed together under strong pressure. By way of example, the illustration of FIG. 2 could be a section of a component corresponding to the first analysis region AB1 of the illustration in FIG. 1. FIG. 3 elucidates an associated material property profile, which is plotted over the component thickness (or analysis region thickness) in the z-direction. The ordinate of the diagram shows, in abstract dimensions, the respectively established fiber volume portion per analysis layer plotted as a measured value. The resultant periodic variation, which, with the maxima and minima thereof, very clearly reproduces points with a high fiber volume portion and points with a low fiber volume portion, can easily be identified from the diagram such that interstices between woven fabric plies can be deduced from this measurement at the points of the lowest fiber volume portion.

Figure 5:
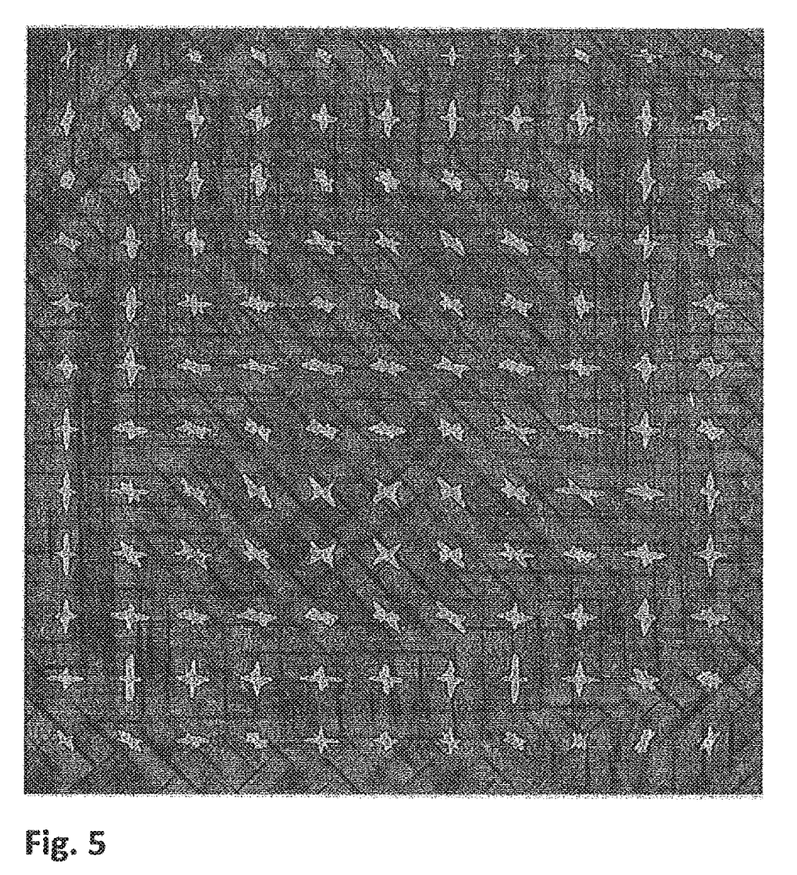
FIG. 5 shows a plan view-histogram representation on a component section.

By selecting a plurality of adjoining analysis regions, a whole component can thus be scanned sectional plane by sectional plane; the corresponding local material properties can be established ply-by-ply and it is thus possible to obtain a separation of the plies over the whole component. By way of example, the result can be a histogram representation of the whole component, which reproduces the respective specific ply orientation of the component. Such an illustration is reproduced in FIG. 5 in an exemplary manner, said figure showing a plan view of a component, composed of woven fabric mats, with a local directional histogram placed thereon. One directional histogram (for one layer) is depicted for each (in this case square) analysis region, said directional histogram being a polar illustration of the frequency of the established direction distributions. The more a histogram representation extends, the more pronounced the collected directions are. A punctiform or circular appearance indicates a very high level of homogeneity of the directional result, while an elliptic representation indicates an associated direction orientation which becomes ever more pronounced, the longer the main axis of the ellipse is. A cross-shaped illustration indicates the presence of two (main) directions, a star-shaped appearance indicates correspondingly more directions, wherein the associated axes specify the respective orientation. Below the histogram representation, it is possible to identify a CT slice image of the component as underlying layer. Such an illustration allows a skilled observer to very quickly detect the established fiber orientations.

Figure 4:
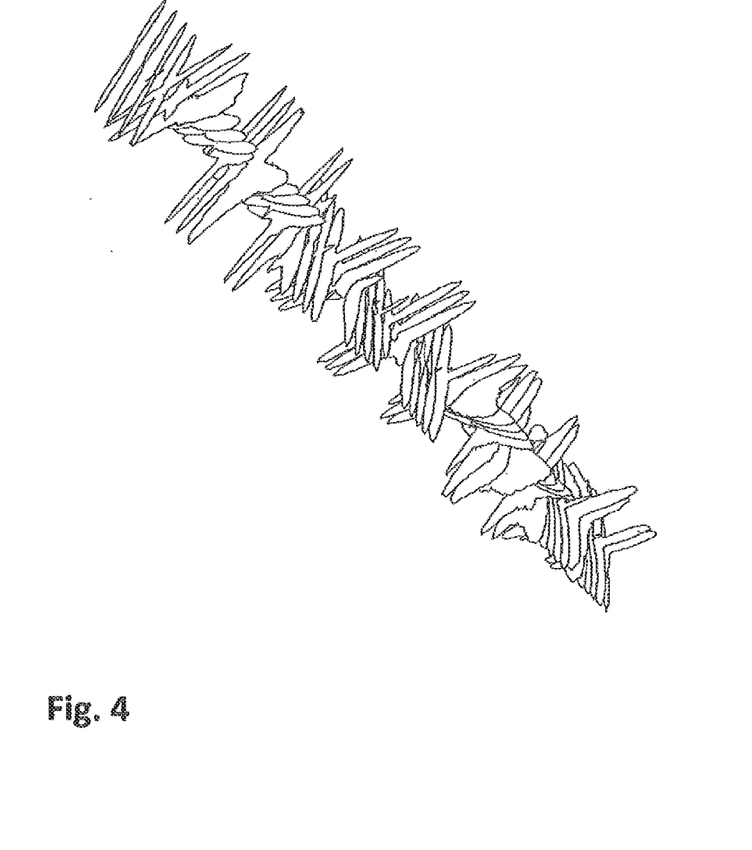
FIG. 4 shows a perspective view of a layer sequence in a histogram representation, based on measured values determined according to the invention.

FIG. 4 shows, in a perspective view, a similar histogram representation of a whole sequence of analysis layers, which in turn establish conclusions for the observer about the dimensions of the established direction(s) and the homogeneity thereof in each analysis layer.

In the illustration of FIG. 1, three further analysis regions AB2, AB3 and AB4 are singled out in an exemplary manner (for the purposes of analyzing the whole component, the whole component section is subdivided into adjoining analysis regions with suitable dimensions).

This exemplary selection of further analysis region serves to elucidate the selection of the size of the individual analysis regions. Thus, for example, the second analysis region AB2 lies in a component section with relatively large curvature, which is why the lateral extent of the analysis region AB2 and the analysis layers 200 thereof are selected to be much smaller, for example, than those of the first analysis region AB1 discussed above. The third analysis region AB3 again lies in a region with a smaller ply curvature, which is why the size of this third analysis region AB3, the analysis regions thereof 300, again has been selected to have an order of magnitude comparable with that of the first analysis region AB1. The fourth analysis region AB4 lies in a section in which, although there is a high ply curvature, the coordinate system is adapted to this curvature by the selection of curved analysis layers 400, which is why a relatively large "pooling region" is possible, and so the analysis region AB4 is selected to be comparatively large at this point despite the curved component form.

Since no ideal ply conditions set in in the real component, but instead it is very often possible to observe a ply drift, i.e. a production-caused displacement of the plies with respect to one another, which leads to the individual woven or laid fabric plies being able to present themselves in each direction of extent of the component with a modified orientation, processing of adjacent analysis regions is furthermore provided according to the invention. Taking into account the analysis regions adjoining one another, for example by interpolation or extrapolation, taking into account smoothness, continuity of the ply structure or similar exemplary assumptions or else targeted re-measuring of detail regions or transition regions leads to a significant stabilization of the individual results. Hence, the separation of the plies over the whole component becomes even more detailed. In this context too, the a priori knowledge about the basic structure of the component already mentioned above can also be included in the calculation.

According to the invention, it is possible to set the applied local coordinate system for aligning the analysis layers by proceeding from a first scanning result of the component for determining the rough direction of extent of the ply. Alternatively, the local coordinate system can be matched/adapted to the real structure (adaptive coordinate system) by proceeding from an initial estimate of the ply structure, from data from a so-called simulation mesh, etc.

The analysis region is selected in such a way that it is a sensible integration range for the subsequent calculation of the material properties. This also relates, in particular, to the size, i.e. the lateral extent, of the analysis region. The size can also be set in interaction with the adaptive coordinate system (within the meaning of optimization calculation on the basis of setting the axes and the size extent).

The invention claimed is:

1. An apparatus for examining a component comprising laid fiber composite fabrics or woven fiber composite fabrics which comprise a number of thin plies with in part different alignment, comprising:
   a measuring device for carrying out a non-destructive measurement to collect volumetric data of the component; and
   an evaluation device for evaluating the collected data of the component, wherein evaluation by the evaluation device comprises selecting a first analysis region in the collected data of the component, determining a local coordinate system of the first analysis region, successively establishing local material properties of the component layer-by-layer at predetermined distances in a relative direction perpendicular to a lateral extent of the first analysis region, detecting ply boundaries along the established local material properties, and averaging the local material properties in each detected ply.

2. The apparatus as claimed in claim 1, wherein the evaluation device for determining a local coordinate system determines a normal vector relative to a ply or a surface.

3. The apparatus as claimed in claim 1, wherein the evaluation device selects the dimensions of the first analysis region in a manner dependent on a curvature of the first analysis region.

4. The apparatus as claimed in claim 1, wherein the evaluation device generates a profile curve of local material properties from the successive layer-by-layer establishment of the local material properties.

5. The apparatus as claimed in claim 4, wherein the evaluation device for detecting ply boundaries detects discontinuities along the profile curve of the local material properties.

6. The apparatus as claimed in claim 1, wherein the evaluation device weights regions around the detected ply boundaries differently from the plies themselves when averaging the local material properties in each detected ply.

7. A method for examining a component comprising laid fiber composite fabrics or woven fiber composite fabrics which comprise a number of thin plies with in part different alignment, comprising the following steps:
   carrying out a non-destructive measurement to collect volumetric data of the component;
   selecting a first analysis region in the collected data of the component;
   determining a local coordinate system of the first analysis region;
   successively establishing local material properties of the component layer-by-layer at predetermined distances in a relative direction perpendicular to a lateral extent of the first analysis region;
   detecting ply boundaries along the established local material properties;
   averaging the local material properties in each detected ply.

8. The method as claimed in claim 7, wherein the step of determining a local coordinate system comprises determining a normal vector relative to a ply or a surface.

9. The method as claimed in claim 7, wherein the dimensions of the first analysis region are selected in a manner dependent on a curvature of the first analysis region.

10. The method as claimed in claim 7, wherein a profile curve of local material properties is generated from the successive layer-by-layer establishment of local material properties.

11. The method as claimed in claim 10, wherein ply boundaries are detected by detecting discontinuities along the profile curve of local material properties.

12. The method as claimed in claim 7, wherein, in the step of averaging the local material properties in each detected ply, regions around the detected ply boundaries are weighted differently to the plies themselves.

13. The method as claimed in claim 7, wherein the result of an analysis region is adapted taking into account the result of at least one adjacent analysis region.

14. The method as claimed in claim 13, wherein the adaptation of the result is carried out by interpolation or extrapolation.

15. The method as claimed in claim 7, wherein the local material properties are scalars, vectors and/or tensors.

16. The method as claimed in claim 15, wherein the local material properties are selected from the group comprising, grayscale value, standard deviation, variance, orientation, structure tensor, porosity.

17. The method as claimed in claim 7, wherein the averaging is selected from the group comprising, a mean value formation, a calculation of higher moments, a histogram distribution, a distribution calculation.

18. A computer program comprising program code means for carrying out all steps of the method as claimed in claim 7 when the computer program is executed on a computer or a corresponding calculation unit.

19. The computer program as claimed in claim 18, which is stored on a non-transitory computer-readable data medium.

* * * * *